United States Patent [19]

Levine et al.

[11] 4,190,328
[45] Feb. 26, 1980

[54] PROCESS FOR DETECTION OF BLOOD-BORNE PARASITES

[76] Inventors: Robert A. Levine, 31 Pilgrim La., Guilford, Conn. 06437; James V. Massey, III, 80 Driftwood La., Trumbull, Conn. 06610; Stephen C. Wardlaw, 128 Sunset Hill Dr., Branford, Conn. 06405

[21] Appl. No.: 965,591

[22] Filed: Dec. 1, 1978

[51] Int. Cl.² .............................................. G02B 00/00
[52] U.S. Cl. ................................. 350/320; 23/230 B; 128/2 G; 356/246
[58] Field of Search ........ 128/335, 2 F, 2 G, DIG. 2, 128/335, 325, 218 C, 223; 356/246; 198/2 G; 350/320; 23/253, 230; 73/440, 448, 655, 49; 195/10; 210/83; 422/55; 424/3

[56] References Cited

U.S. PATENT DOCUMENTS

| Re. 29,061 | 12/1976 | Bucalo | 128/2 F |
|---|---|---|---|
| 2,586,581 | 2/1952 | Tischischeck | 128/218 C |
| 3,874,851 | 4/1975 | Wilkins et al. | 128/2 F |
| 3,898,982 | 8/1975 | Katsuda | 128/2 G |
| 4,025,306 | 5/1977 | Studer | 128/2 G |
| 4,027,660 | 6/1977 | Wardlaw et al. | 128/2 G |
| 4,060,388 | 11/1977 | Rapp et al. | 356/246 |
| 4,090,795 | 5/1978 | Flossdorf et al. | 356/246 |

*Primary Examiner*—John K. Corbin
*Assistant Examiner*—B. W. de los Reyes
*Attorney, Agent, or Firm*—William W. Jones

[57] ABSTRACT

A process for detecting parasites which are found in the blood of a host. A sample of blood is drawn into a capillary tube which contains a generally cylindrical mass having a specific gravity such that it will float in one of the cell layers when the sample is separated by centrifugation. The specific gravity of the mass is selected so as to cause the cylindrical mass to combine with the bore wall of the capillary tube to form a thin annular space in the capillary tube into which the parasites will be crowded, thus increasing the concentration of parasites in a restricted area of the centrifuged blood sample and rendering the parasites highly visible. A stain may be used to differentially color the parasites. One specific parasite which can be detected in this manner quickly and inexpensively is heartworm.

6 Claims, 1 Drawing Figure

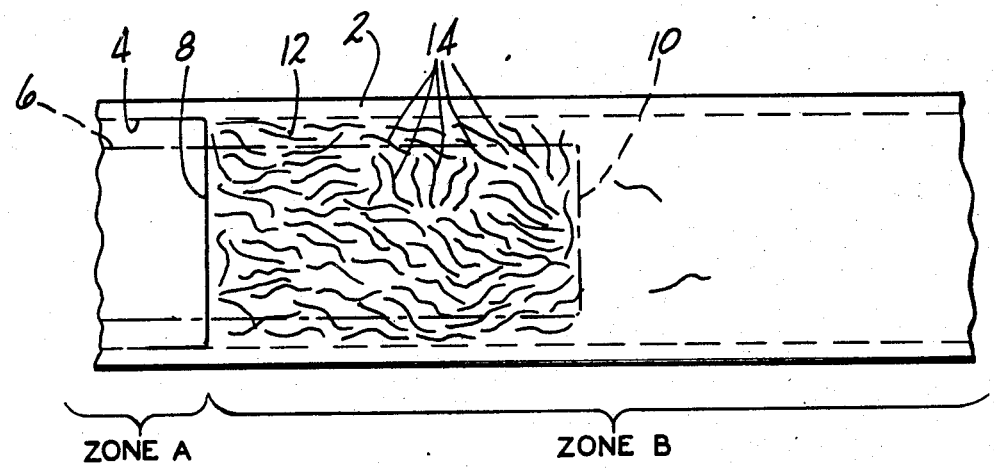

PROCESS FOR DETECTION OF BLOOD-BORNE PARASITES

We have developed a technique for enhancing or elongating a layer of a constituent material in multilayer centrifuged sample of a biological fluid or other complex fluid material. This technique involves the use of an elongated preferably substantially cylindrical body which is positioned within the bore of a capillary tube in which the fluid sample to be tested is drawn. The body has an outside diameter which is a predetermined amount smaller than the bore diameter of the capillary tube so as to form an annular free space between the tube bore wall and the outer surface of the body, within the tube bore. The body is made from a material having a predetermined specific gravity so that, after centrifugation, the body will float upon or slightly in one of the layers of the multi-layered material so that at least one of the layers of less dense material constituents will occupy the annular free space. In this way, the axial extent of such less dense layer or layers will be elongated over that which would occur were the body not in the capillary tube bore. The technique described above is fully set forth in our U.S. Pat. No. 4,027,660, issued June 7, 1977.

We have found that this technique can be used to provide a quick and accurate test for determining whether the blood of a host contains such blood-borne parasites such as microfilariae and trypanosomes. Such parasites have a particular known density which will cause them to congregate in a thin layer in a sample of centrifuged blood. They cylindrical body is made from a material, preferably a resinous material, having a specific gravity approximately equal to or greater than the specific gravity of the parasite, so that after centrifugation, the parasite layer will be crowded into the annular free space. In this manner, the parasite layer will be axially expanded somewhat and the population density of parasites in the layer will be greatly increased. The parasites will thus be rendered readily visible through the capillary tube under optical magnification. The parasites are preferably differentially colored with an appropriate stain, or otherwise rendered more visible. Thus, the method of this invention can be used for early detection of parasitic diseases in man and animals.

One blood-borne parasite which has been detected in blood samples of infected hosts using the process of this invention is heartworm microfilariae.

Heartworm is a parasite which is transmitted by mosquitoes and invades the blood stream of an infestated animal, and can kill the animal if left untreated. Annual checkups should be made of animals to guard against heartworm infestation. The prior art techniques for testing for the presence of heartworm in an animal's blood can be time consuming, expensive, and require the use of substantial equipment. U.S. Pat. No. 4,025,306, issued May 24, 1977 to Arnold David Studer describes one general type of prior art heartworm testing procedure. This procedure is typified by the drawing of a blood sample into a lysing solution which destroys the corpuscular components of the blood. The sample is then treated with a stain which the heartworm microfilariae absorb. The blood sample is then passed through a filter which stops the heartworm microfilariae. The filter is then examined under a microscope for the presence of the microfilariae. This test has proven to be determinative of the infestation in approximately ninety percent of all cases. Thus, the test has about a ninety percent validity. This test is also capable of distinguishing between the microfilariae of the heartworm Dirofilaria immitis and those of Dipetalonema reconditum, a relatively harmless subcutaneous parasite, also found in the blood which the D. immitis microfilariae resemble. It is believed that the filter test is the most accurate and valid test used to detect heartworm at the present time.

Other test procedures have also been proposed and practiced. For example, a blood smear may be applied to a slide and examined under a microscope. In another procedure, a sample is drawn in a capillary tube, lysed, spun down in a centrifuge, and the plasma is then discarded. The residue is stained with an appropriate stain, smeared on a slide and examined under a microscope for the presence of heartworm microfilariae. Yet another procedure involves the drawing of a blood sample into a capillary tube, spinning the tube in a centrifuge, and examining the buffy coat of the centrifuged blood sample for the presence of viable heartworm microfilariae. The viable heartworm microfilariae can be seen moving in the buffy coat of the centrifuged blood sample under optical magnification. This latter procedure is quickly and easily performed; however, it is difficult with this procedure to distinguish the D. immitis microfilariae from the D. reconditum microfilariae. The main differences between the live dangerous D. immitis microfilariae and the live relatively harmless D. reconditum microfilariae are that the former are present in the samples in greater concentration than the latter, and the former undulate in one place within the blood sample, while the latter undulate and propel themselves through the blood sample. Other physical differences such as the tapered head and straight tail of the D. immitis, and the blunt head and buttonhook tail of the D. reconditum will not be observed in the living microfilariae, as they would in a stained lysed smear.

We have discovered that the first above-described techniques of material layer enhancement developed by us for differential measurement of biological fluids can be used to detect the presence of live heartworm microfilariae in a sample of anticoagulated canine blood. The blood sample is drawn into a capillary tube which also contains a preferably generally cylindrical body which is made from a resinous material having a specific gravity in the range of 1.02 to 1.09. After centrifugation, the resinous body floats on the blood sample red cell layer and preferably occupies about 75% or more of the space in the tube bore in which the buffy coat settles. Thus, the body combines with the wall of the tube bore to form an annular space into which the buffy coat settles, thereby elongating the physical boundaries of the buffy coat. The heartworm microfilariae also settle into the annular space in an annular narrow band. Since the band is annular and of comparatively small radial thickness, all of the heartworm microfilariae are confined in a radially thin band directly adjacent to the transparent tube bore wall, thus their presence and activity are much more readily discernable than if they were able to enter into the central portion of the layer which they occupy within the tube. Thus, the heartworm microfilariae layer will be axially expanded, and more concentrated in number, than with the prior art living preparation procedures.

It is, therefore, an object of this invention to provide a quick and accurate method for detecting the presence of blood-borne parasites in a blood sample of a host.

It is a further object of this invention to provide a method of the character described which utilizes a prepared capillary tube and volume-occupying insert for containing the blood sample being tested.

It is yet another object of this invention to provide a method of the character described wherein the population density of the parasite is increased in a centrifuged sample of blood to render the parasite more easily detectable.

It is an additional object of this invention to provide a method of the character described which can be quickly and easily performed without the necessity of using special procedures to prepare microscope slides or the like.

These and other objects and advantages of this invention will become more readily apparent from the following detailed description of a preferred embodiment of the invention taken in conjunction with the accompanying drawing which is a fragmented top plan view of a portion of a capillary tube showing the appearance of heartworm microfilariae under magnification.

Referring to the drawing, there is shown a portion of a capillary tube 2 which contains a centrifuged sample of canine blood which is infested with heartworm microfilariae. The bore wall of the tube 2 is denoted by the numeral 4 and there is disposed in the tube bore 4 a generally cylindrical body 6 (shown for clarity purposes in phantom). The transverse line 8 denotes the interface between the granulocyte layer of the buffy coat which is in Zone A of the drawing, and the red cell layer, which is in Zone B of the drawing. It will be noted that the body 6 sinks somewhat into the red cell layer after centrifugation so that the end surface 10 of the body 6 is offset within the red cells from the granulocyte-red cell interface 8. The body 6 being disposed within the tube bore 4 creates a restricted annular space 12 within the tube 2 which is completely visible through the glass tube into which the buffy coat cells of the centrifuged blood sample are crowded, and into which a portion of the red cells of the centrifuged blood sample are crowded, i.e., the lightest portion of the red cells. The heartworm microfilariae have a specific gravity or density which is approximately the same as the corresponding value of the granulocytes and the lightest fraction of the red cells. Therefore, during centrifugation, whatever heartworm microfilariae which may be present in the blood sample are centrifuged into the general zone containing the granulocytes and lightest red cells. Since this zone is also occupied by the body, the microfilariae are forced into the restricted annular space 12, as will be seen from the drawing, the microfilariae being identified by the numeral 14. By forcing the microfilariae into the restricted annular space, the population density of the microfilariae per unit volume of blood is greatly increased whereupon their presence in the sample is easily visibly detected. It will be noted that beyond the end surface 10 of the body 6 very few microfilariae will be detected in the red cells due to the greater volume of space for them to be found in within the tube, and due to the masking ability of the red cells. In order to render the heartworm microfilariae even more visible, a stain, such as acridine orange is added to the blood sample, which stain is absorbed by the microfilariae and causes them to fluoresce when exposed to proper wavelengths of illuminating light. Moreover, the red cells do not fluoresce so that the fluorescing microfilariae will be starkly highlighted against a black background of red cells. This improved highlighting of the microfilariae makes it possible to distinguish the harmful D. immitis strain which characteristically undulates in one place within the sample, from the benign D. reconditum which undulates and propels itself through the blood sample. Naturally, if the animal from which the blood sample is taken is not infected, there will be no microfilariae seen in the centrifuged sample of blood.

A specific example of the method of this invention is generally as follows. Approximately 110 lambda ($\lambda$) of blood, either venous blood from a standard EDTA-containing evacuated container, or capillary blood obtained by a cutaneous puncture, is drawn into a capillary tube, the bore of which has been dry coated with about 50 micrograms of acridine orange stain and 167 micrograms of EDTA. The dry coating of EDTA is put in the tubes to adapt the tubes for direct filling from the cutaneous puncture procedure. The tube bore is 0.08749 inch in diameter. A cylindrical float of Rexolite, which is a cross-linked styrene, having a diameter of 0.083 inch and a specific gravity of about 1.043 is then placed in the tube and the tube is centrifuged in a conventional capillary tube centrifuge for about 4 minutes. The acridine orange stain is taken up by the white cells and any microfilariae present in the blood sample.

The centrifuged tube is then observed under $50-100\times$ magnification with trans or epi-illumination of the tube with a suitable wavelength light source so as to cause the acridine orange stain, and the organisms which have absorbed it, to fluoresce.

The cylindrical float will sink into and float in the red cell layer of the centrifuged blood sample and continue up through the buffy coat and into the plasma. Any heartworm microfilariae present in the sample will fluoresce and will be centrifuged into a relatively narrow band extending down into the portion of the red cell layer, occupied by the least dense red cells and up somewhat into the granulocyte layer of the buffy coat. Due to the presence of the float in the red cells and buffy coat, any heartworm microfilariae present in the blood sample will be crowded into the narrow annular space between the outer surface of the float and the tube bore wall, whereby the population density of the microfilariae will be greatly increased rendering detection of the parasites much quicker and easier to achieve. The microfilariae in the red cell layer will be readily visible as brightly fluorescing bodies starkly contrasted to the black non-fluorescing red cell background. The characteristic in-place undulation of the D. immitis microfilariae is readily observed using the process of this invention, as previously noted.

As previously noted, while the specific examples described above relating to the method of this invention relate to the detection of heartworm microfilariae in a blood sample, the method can also be used to detect other blood-borne parasites. The specific gravity or density of the particular parasite must be known so that a compatible material can be used for the insert body. In this manner, the method of this invention has vast application in the early detection and treatment of blood-borne parasitic diseases. The test can be done inexpensively with paraphenalia which has been pretreated with the necessary reagents. Additional equipment needed is a conventional capillary tube centrifuge and an appropriate viewing instrument. In lieu of a stain, the parasites can be highlighted within the blood sample through the use of a fluoresceine or other fluorescent stain tagged antibody which is specific for the given parasite being looked for. The tagged antibody may be dry-coated on the tube bore wall, or may be pre-mixed with the blood sample. The tagged antibodies will attach themselves to the parasites, if the latter are present in the blood sample, and form a fluorescent band in the centrifuged blood sample. Minor background fluorescence will also occur.

Since many changes and variations of the disclosed embodiment of the invention may be made without departing from the inventive concept, it is not intended to limit the invention otherwise than as required by the appended claims.

What is claimed is:

1. A method for visually detecting the presence of a particular parasite in a sample of anticoagulated blood, said method comprising the steps of:
   (a) substantially filling a transparent capillary tube with a sample of whole blood to be tested for parasite infestation;
   (b) centrifuging said blood sample in said tube to cause any parasites present in said blood sample to settle into a defined layer due to the specific gravity of the parasites;
   (c) providing a generally cylindrical body in said capillary tube during said centrifuging step to form a narrow annular free space within said tube, said free space being radially bounded inwardly by the outer surface of said body and outwardly by the bore wall of said tube into which free space at least a significant portion of said layer of the parasites settles during centrifugation whereby the population density of said portion of said layer of parasites is substantially increased to render the presence of parasites in the blood sample readily discernable under appropriate optical magnification; and
   (d) differentially highlighting the parasites in the blood sample to render the parasites highly visible with respect to surrounding blood cell types.

2. The method of claim 1, wherein the parasites are highlighted by adding a stain to the blood sample which stain is absorbed by the parasites.

3. The method of claim 2, wherein at least a portion of the parasites are centrifuged into the red blood cell layer of the blood sample.

4. The method of claim 1, wherein the parasites are highlighted by adding an effective amount of a fluorescent antibody to the blood sample, which antibody is specific to the parasites being tested for.

5. A method for visually detecting the presence of a particular parasite in a sample of anticoagulated blood, said method comprising the steps of:
   (a) substantially filling a transparent capillary tube with a sample of whole blood to be tested for parasite infestation;
   (b) centrifuging said blood sample in said tube to cause any parasites present in said blood sample to settle into a defined layer due to the specific gravity of the parasites;
   (c) providing a generally cylindrical body in said capillary tube during said centrifuging step to form a narrow annular free space within said tube adjacent to the bore wall of said tube, into which free space said defined layer of parasites will settle whereby the population density of the parasites within said defined layer is greatly increased;
   (d) introducing a colorant into said blood sample which colorant is operable to differentially color the parasites; and
   (e) subjecting said centrifuged blood sample contained in said tube to optical magnification to determine the presence or absence of parasites therein.

6. A method for visually detecting the presence of a particular parasite in a sample of anticoagulated blood, said method comprising the steps of:
   (a) substantially filling a transparent capillary tube with a sample of whole blood to be tested for parasite infestation;
   (b) centrifuging said blood sample in said tube to cause any parasites present in said blood sample to settle into a defined layer due to the specific gravity of the parasites;
   (c) providing a generally cylindrical body in said capillary tube during said centrifugation step to form a narrow annular free space within said tube adjacent to the bore wall thereof, into which free space said defined layer of parasites settles during centrifugation whereby the population density of the parasites within said defined layer is greatly increased;
   (d) providing an effective amount of a fluorescent antibody in said blood sample which antibody is specific to the parasite being tested for, said antibody being operable to attach to the parasites to render the parasite layer differentially fluorescent from the remainder of the blood sample; and
   (e) subjecting the centrifuged blood sample in the tube to optical magnification to determine the presence or absence of parasites.

* * * * *